United States Patent
Hung et al.

(10) Patent No.: US 6,629,936 B2
(45) Date of Patent: Oct. 7, 2003

(54) METHOD AND KITS FOR DIFFERENTIATING BREAST DUCTS FOR CANCER RISK STATUS

(75) Inventors: David Hung, Belmont, CA (US); Susan Love, Pacific Palisades, CA (US)

(73) Assignee: Cytyc Health Corporation, Boxborough, MA (US)

( * ) Notice: Subject to any disclaimer, the term of this patent is extended or adjusted under 35 U.S.C. 154(b) by 0 days.

(21) Appl. No.: 09/852,145

(22) Filed: May 10, 2001

(65) Prior Publication Data

US 2002/0007115 A1 Jan. 17, 2002

Related U.S. Application Data

(60) Provisional application No. 60/289,536, filed on May 9, 2001, and provisional application No. 60/203,416, filed on May 10, 2000.

(51) Int. Cl.$^7$ ................................. A61B 5/00
(52) U.S. Cl. ....................... 600/573; 604/74
(58) Field of Search ................. 600/573, 584, 600/362, 363, 562; 604/74, 514; 435/7.23, 7.1

(56) References Cited

U.S. PATENT DOCUMENTS

| | | | |
|---|---|---|---|
| 3,608,540 A | | 9/1971 | Sartorius |
| 6,168,779 B1 | * | 1/2001 | Barsky et al. ............ 424/9.2 |
| 6,221,622 B1 | * | 4/2001 | Love ...................... 435/7.23 |
| 6,287,521 B1 | * | 9/2001 | Quay et al. ............. 422/101 |
| 6,328,709 B1 | * | 12/2001 | Hung et al. ............. 604/74 |

FOREIGN PATENT DOCUMENTS

| WO | WO 99 13917 | 3/1999 |
|---|---|---|
| WO | WO 99 55384 | 11/1999 |

OTHER PUBLICATIONS

Petrakis, "Studies on the Epidemiology and Natural History of Benign Breast Disease and Breast Cancer Using Nipple Aspirate Fluid", Cancer Epidemiology, Biomarkers and Prevention, vol. 2, pp 3–10, Jan./Feb. 1993.

Petrakis, "Nipple Aspirate Fluid in Epidermiological Studies of Breast Disease", Epidemiologic Reviews, vol. 15 (1), pp 188–195, 1993.

Sauter et al., "Nipple Aspirate Fluid: A Promising Non–Invasive Method to Identify Cellular Markers of Breast Cancer Risk", British Journal of Cancer, vol. 76 (4), pp 494–501, 1997.

Sartorius, Breast fluid cells help in early cancer detection, JAMA vol. 224 (6), pp 823–827, 1973.

Papanicolaou et al, Exfoliative Cytology of the Human Mammary Gland and Its Value in the Diagnosis of Cancer and Other Diseases of the Breast, Cancer, vol. 11, pp 377–409, Mar./Apr. 1958.

Goodson et al, "Discharges and Secretions of the Nipple", The Breast: Comprehensive Management of Benign and Malignant Diseases, $2^{nd}$ Ed. vol. 2, Bland & Kirby eds., pp 51–74. 1998.

Sartorius et al., Cytologic Evaluation of Breast Fluid in the Detection of Breast Disease, Journal of the National Cancer Institute, vol. 59(4), pp 1073–1080, 1977.

King et al, Nipple Aspirate Cytology for the Study of Breast Cancer Precursors, Journal of the National Cancer Institute, vol. 71(6), pp. 1115–1121, 1983.

Wrensch, Breast Cancer Incidence in Women with Abnormal Cytology in Nipple Aspirates of Breast Fluid, Am. J. Epidemiology, vol. 135(2), pp 130–141.

* cited by examiner

Primary Examiner—Charles A. Marmor, II
(74) Attorney, Agent, or Firm—Banner & Witcoff, Ltd.

(57) ABSTRACT

Differentiating breast ducts for cancer risk status is a key element in a procedure to screen women for breast cancer. The 6 to 9 breast ducts on the human breast can be differentiated to identify those of higher risk for cancer. The higher risk ducts merit access and analysis of the ductal fluid and monitoring and/or treatment.

32 Claims, 3 Drawing Sheets

US 6,629,936 B2

METHOD AND KITS FOR DIFFERENTIATING BREAST DUCTS FOR CANCER RISK STATUS

Benefit of the May 10, 2000 filing date of Provisional Application Serial No. 60/203,416 and benefit of the May 9, 2001 filing date of Provisional Application Serial No. 60/289,536, both provisionals by the same inventors and both entitled "Method For Differentiating Breast Ducts For Cancer Risk Status" are hereby claimed.

BACKGROUND OF THE INVENTION

It is believed that breast cancer begins in the breast milk ducts and it is known that the human breast has from about 6 to 9 ducts. Emerging technology is providing systems, kits, methods and devices for collecting fluid from these ducts individually so as to keep separate the material collected from each duct and to analyze it separately. Copending and co-owned applications to methods and kits for obtaining fluid and cellular material from breast ducts, U.S. Ser. No. 09/067,661 filed Apr. 28, 1998 now U.S. Pat. No. 6,221,622, and its CIP U.S. Ser. No. 09/301,058 filed Apr. 28, 1999, now U.S. patent application Publication No. 2002/0019017 describe and claim infusing fluid into the duct and collecting the fluid using a catheter.

Previously it has been found that breasts that yielded fluid upon nipple aspiration identified the patient as being at risk for developing breast cancer. See Petrakis, "Studies on the epidemiology and natural history of benign breast disease and breast cancer using nipple aspirate fluid" *Cancer Epidemiology, Biomarkers and Prevention* (January/February 1993) 2:3–10; Petrakis, "Nipple Aspirate Fluid in epidemiological studies of breast disease", *Epidemiologic Reviews* (1993) 15:188–195. In addition, pooled nipple aspirate fluid has been analyzed for cancer markers. See Sauter et al, "Nipple aspirate fluid: a promising non-invasive method to identify cellular markers of breast cancer risk", *British Journal of Cancer* 76(4):494–501 (1997).

Upon identification of a duct that may have abnormal cells by analysis of the ductal fluid, that duct can be targeted for breast sparing treatment including administering an agent intraductally to the duct, rather than systemically, or removing just the affected duct. In order to review the entire breast by this method, however, all 6 to 9 ducts on the breast must be identified and accessed, which is a difficult and time consuming task, and for these reasons accessing all the ducts on a breast in order to perform a diagnosis remains a suboptimal strategy.

There is thus a need in the art to develop techniques to identifying ducts that are at higher risk for cancer than other ducts on the same breast so that fewer than all the ducts on the breast can be targeted for access and analysis. The present invention provides such a solution to this problem.

SUMMARY OF THE INVENTION

It is an object of the invention to provide methods for differentiating a cancer risk status of milk ducts in a breast.

It is another object of the invention to provide kits for differentiating a cancer risk status of milk ducts in a breast.

These and other objects of the invention are provided by one or more of the embodiments described below. In one embodiment a method of differentiating a cancer risk status of milk ducts in a breast comprises aspirating the nipple, and locating at least one ductal orifice that yields fluid upon aspiration; wherein a duct that yields fluid upon aspiration is at higher risk for cancer. More than one duct can yield fluid at the orifice upon aspiration of the nipple. The method can further comprise accessing a ductal orifice that yields fluid; retrieving ductal contents from the accessed duct; recording the location of the ductal orifice once identified by yield of fluid at the orifice; and/or making an identifiable mark at the ductal orifice upon yield of fluid at the orifice. Recording can comprise one or more of transcribing the relative location of the orifice onto a paper grid, taking a photograph, recording in real time on a digital screen the fluid yielding event and/or location of the ductal orifice that yielded fluid, and making a negative imprint on the nipple surface to identify the regions of the nipple that did not yield fluid. Marking can comprise making an identifiable mark with a pen or other labeling device to identify the spot comprising the ductal orifice at a later time; and/or placing an element into the duct such as a plug, tube, wire, thread or suture. The mark can reside on the nipple surface in a range of time from a few hours to a few years. The method can further comprise contacting a ductal orifice that yields fluid with a dilator in order to accomplish one or more of discerning the precise location of the orifice, discerning the orientation of the orifice, or enlarging the proximal area of the duct so as to facilitate subsequent cannulation of the duct.

Another embodiment of the invention provides a method of differentiating a cancer risk status of milk ducts in a breast comprising aspirating the nipple, and locating at least one ductal orifice that yields fluid upon aspiration; wherein a duct that yields fluid upon aspiration is at higher risk for cancer; and collecting a bead of fluid at the nipple surface generated from aspiration and emerging from the fluid yielding duct and not mixed with fluid generated from any other fluid yielding ducts on the nipple surface. The method can further comprise analyzing the collected fluid of the duct yielding fluid separately from the fluid of any other duct yielding fluid; marking the duct that yields fluid; and/or recording the location of the ductal orifice once identified by yield of fluid at the orifice. Recording can comprise one or more of transcribing the relative location of the orifice on a paper grid, taking a photograph, recording in real time on a digital screen the fluid yielding event and/or location of the ductal orifice that yielded fluid, and making a negative imprint on the nipple surface to identify the regions of the nipple that did not yield fluid. Marking can comprise making an identifiable mark with a pen or other labeling device to identify the spot comprising the ductal orifice at a later time; and/or placing an element into the duct such as a plug, tube, wire, thread or suture. The mark can reside on the nipple surface in a range of time from a few hours to a few years. The method can further comprise contacting a ductal orifice that yields fluid with a dilator in order to accomplish one or more of discerning the precise location of the orifice, discerning the orientation of the orifice, or enlarging the proximal area of the duct so as to facilitate subsequent cannulation of the duct Embodiments including kits for differentiating a cancer risk status of milk ducts in a breast can comprise a nipple aspiration device, a system to mark and/or record the location of an orifice that yields fluid upon aspiration, and instructions for use of the kit to differentiate a cancer risk status of milk ducts in a breast by aspirating the nipple and locating at least one ductal orifice that yields fluid upon aspiration. Such a kit can further comprise a ductal access tool and further instructions to access the duct that yields fluid upon nipple aspiration. The system to mark and/or record the location of the ductal orifice that yields fluid can comprise one or more of a pencil and paper grid, a camera, a marking tool, a digital recording and imaging device, a system to make a negative imprint on the nipple surface, and an element to place in the orifice to mark it. The kit may also comprise a dilator. Another kit for differentiating a cancer risk status of milk ducts in a breast can comprise a nipple aspiration device, ductal access tool to access a duct through an orifice that yields fluid upon aspiration, and instructions for use of the kit to differentiate a cancer risk status of milk ducts in a breast by aspirating the nipple, including instructions to locate at least one ductal orifice that yields fluid upon aspiration, and access that duct through its orifice. Optionally the kit can also comprise a dilator.

Another kit for differentiating a cancer risk status of milk ducts in a breast can comprise a nipple aspiration device, a tool to collect an emerging bead of fluid at a ductal orifice, without mixing the collected fluid with any other fluid yielded from any other duct, and instructions for use of the kit to differentiate a cancer risk status of milk ducts in a breast by locating at least one ductal orifice upon aspiration of the nipple and instructions to collect a bead of fluid from that ductal orifice at the nipple surface without mixing the collected fluid with any other fluid yielded from any other duct on the nipple surface. Such a kit can further comprise means and instructions for analyzing any collected ductal fluid for making a determination of cancer risk in that duct. All kits can further comprise a container for the kit contents.

It is an object of the invention to maximize the likelihood of ductal fluid migrating to the nipple surface upon nipple aspiration. Accordingly, there is provided a method of maximizing the likelihood of ductal fluid migrating to the nipple surface upon nipple aspiration comprising stimulating the breast and/or nipple surface prior to or during nipple aspiration. Stimulating can comprise placing a wearable device in contact with the nipple surface.

DETAILED DESCRIPTION OF THE EMBODIMENTS

Figure 1:
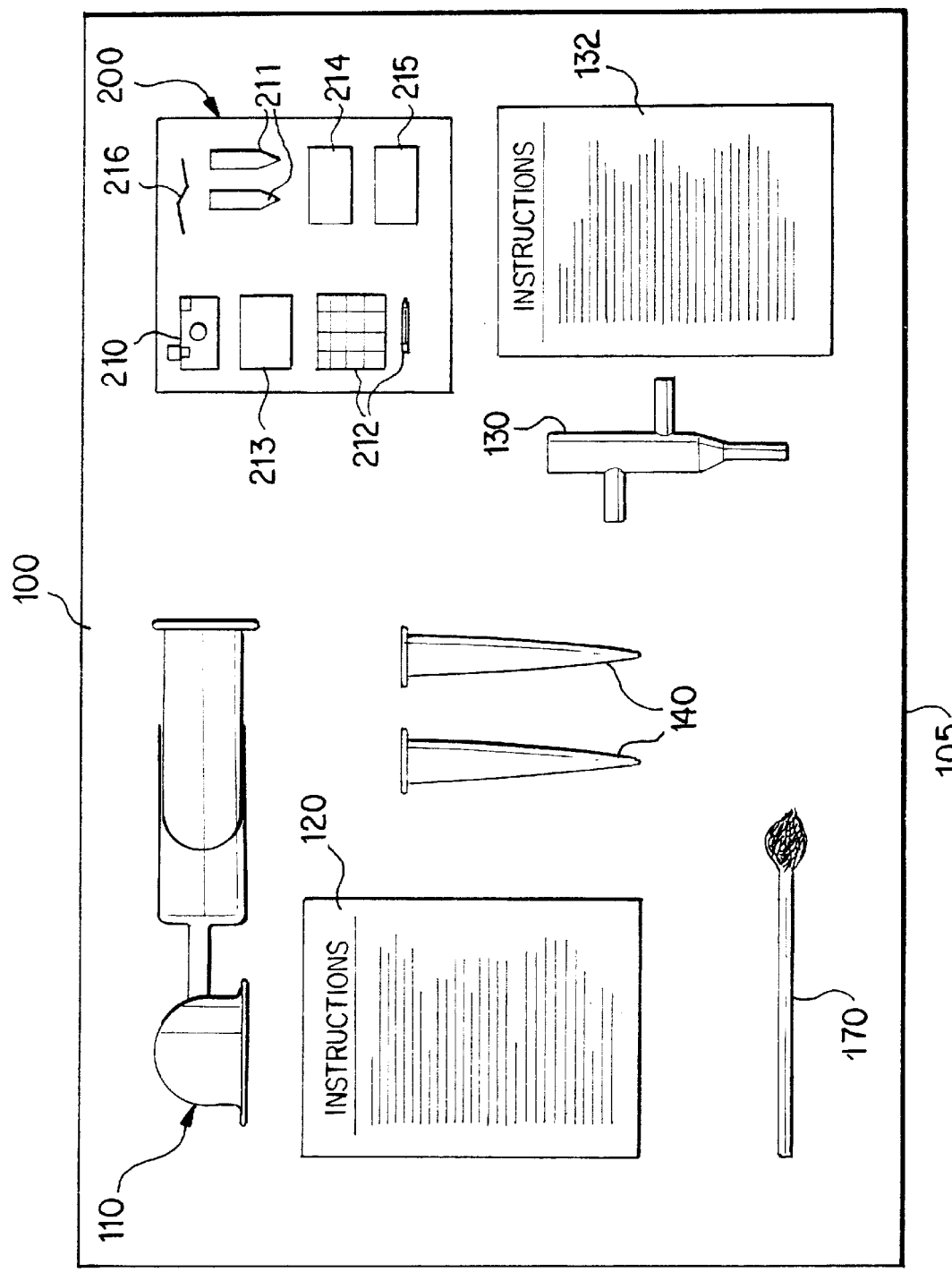
FIG. 1 illustrates a first embodiment of a kit for differentiating between a cancer risk status of a breast duct according to the present invention.

It is a discovery of the invention that breast ducts on a human breast nipple which are at higher risk for cancer can be differentiated from those ducts which are at lower risk. After identification of the higher risk ducts these ducts can then be marked and/or their location recorded e.g. for purposes of facilitating subsequent location and access. Marking can facilitate locating the higher risk duct or ducts later for access, treatment or monitoring. The higher risk ducts can be accessed and their ductal contents analyzed for abnormal cells or other markers that would indicate cancer or cancer precursors. If cancer is identified in a duct, it is marked and can be treated and/or monitored. Thus, differentiating a cancer risk status of breast ducts of a breast includes determining which of the 6 to 9 breast ducts on the breast is most or more likely to have carcinoma or other cancer or the precursors of carcinoma or other cancer, and therefore should be analyzed for the presence of cancer marker in the contents of the ductal fluid.

Breast cancer is believed to originate in the lining of a single breast milk duct in the breast; and additionally human breasts are believed to contain from 6 to 9 of these ducts. See Sartorius, *JAMA* 224 (6): 823–827 (1973). It is now generally believed that the human breast has from 6 to 9 milk ducts which begin at the ductal orifices on the nipple surface and which extend and branch in the breast until the ductal lumens reach and become the terminal ductal lobular unit (TDLU) at the base of the breast. Breast cancer is believed to begin in the milk ducts, and the ductal carcinoma or carcinoma in the TDLU can be in situ or the carcinoma can be invasive. In the early stages of breast cancer it is likely that not all 6 to 9 ducts are affected but rather a duct or a number of ducts something less than the total number of ducts have carcinoma and the rest are unaffected. As such it would be advantageous to the medical community and patient population to be able to identify the ducts that are more likely to have carcinoma, and from which ductal fluid should be collected for analysis.

The method is practiced by aspirating the nipple on the target breast. Nipple aspiration has been used to retrieve ductal fluid for analysis of fluid pooled from all or any yielding ducts in the target breast. Nipple aspiration can be accomplished by placing an aspiration cup on the nipple and generating a negative pressure or vacuum on the nipple surface to encourage any fluid within the ducts to come to the surface of the nipple. The aspiration device can resemble a breast pump used by lactating mothers to retrieve breast milk. Aspiration can be accomplished essentially as described in co-pending and co-owned U.S. patent application Ser. No. 09/438,219 filed Nov. 12, 1999, now U.S. Pat. No. 6,328,709. Aspiration can also be accomplished as described in Papanicolaou et al, "Exfoliative Cytology of the Human Mammary Gland and Its Value in the Diagnosis of Cancer and Other Diseases of the Breast" Cancer (1958) March/April 377–409 Papanicolaou et al (1958) *Cancer,* 11:377–409; Goodson W H & King E B, *Chapter 4: Discharges and Secretions of the Nipple,* The Breast: Comprehensive Management of Benign and Malignant Diseases (1998) $2^{nd}$ Ed. vol 2, Bland & Kirby eds. W. B. Saunders Co, Philadelphia, Pa. pp. 51–74; Sartorius et al (1977) *Journal of the National Cancer Institute* 59(4):1073–80; King et al, (1983) *Journal of the National Cancer Institute* 71(6):1115–21; Wrensch et al, (1992) *Am. J. Epidemiology,* v. 135 (2): 130–141. See also generally, The Breast: Comprehensive Management of Benign and Malignant Breast Diseases, Bland and Copeland eds. W. B. Saunders Co. Philadelphia Pa. 1991 pages 61–67. The nipple aspiration process can be repeated several times until fluid is yielded. In addition, fluid yield may be facilitated by massaging and/or squeezing the breast before or during the aspiration, or by other techniques such as the application of heat to the breast before or during the aspiration procedure.

Nipple aspiration will result in yield of fluid at at least one duct on the nipple surface in some women. During the process of locating a ductal orifice that yields fluid upon aspiration, it is important to identify the small amount of fluid coming from the ductal orifice as early in the aspiration procedure as possible. In this way, the droplet or bead developing at the particular orifice is linked directly to the duct yielding the fluid and not confused with any other ducts that are also yielding fluid or any other topography on the nipple surface that could be mistaken for an orifice. The location on the nipple surface from which the fluid first comes forward to the surface is presumed to be the location of the ductal orifice on that nipple surface. The nipple surface has an uneven topography with much layered skin and other contours so that orifice identification can be difficult without the presence of an indicator such as a small unit of fluid that is perhaps a bit shinier than the nipple surface and therefore distinguishable from the rest of the surface that is not yielding fluid. More than one duct can yield fluid on the nipple surface during a nipple aspiration procedure. In that case, an opportunity is presented to locate more than one duct by identifying the ductal orifice at which the fluid is appearing or emerging. More than one or multiple ductal orifices can yield fluid during aspiration, be marked and/or recorded for the location of the orifice, and/or be accessed as described herein.

As such the location can be recorded or marked or otherwise identified at the first sign of fluid yield. One simple means of identifying the location where the fluid first comes onto the nipple surface is to use the naked eye, or a magnification tool such as a loupe or microscope. Once it is believed that the ductal orifice is located, since it would be easy to forget or loose track of the exact position of the orifice, the nipple surface can be marked, or the location of the orifice can be otherwise recorded for re-identification of the location of the orifice later. Marking can be making an identifiable mark on the nipple surface, e.g. with a pen or other marker. The mark on the nipple surface can be read using visible light, or may be UV light sensitive, etc. Recording the location of the orifice can be accomplished for example, by marking the relative position of the orifice on graph paper or other grid using a pencil or pen, for example orienting the breast and nipple on a north-south-east-west axis and marking the location of the orifice relative to these axis and/or other landmarks on the breast, nipple or patient. Marking can also be accomplished by marking by taking a photograph of the nipple (e.g. before, after and during fluid yield), or recording the process of fluid yield in real time with an analog or digital video camera so that the fluid yield is documented and recorded on a digital screen. Additionally, for example, a negative imprint on the nipple surface can be made to identify the regions of the nipple that did not yield fluid, in order to particularly highlight the very small regions that did yield fluid. Marking the ductal orifice can also be accomplished by placing an element in the duct once it is identified, e.g. a plug, tube, wire, thread or suture, etc into the duct. The element can be seen at the nipple surface to identify the orifice later. Also, having a physical element in the duct can facilitate ductal access later if desired, for example a tube that can provide a channel for accessing the duct, or a wire that keeps the duct open until the practitioner can access it.

In any event the mark made at the orifice or around the orifice is an identifiable mark made so that the orifice can be identified at some time later. For example, one or more orifices yield fluid upon aspiration and are marked. Each one can then be accessed in turn and fluid retrieved from each duct is kept separate and analyzed separately. The identifiable mark can be made with a pen (e.g. a pen for human skin) or other labeling device to identify the spot on the nipple surface at which the ductal orifice is located. The labeling can last a short time or a long time depending on the needs of the practitioner and/or the patient. For example, the mark can remain until washed off with water or alcohol or other effective solvent (e.g. about an hour or two or a half or full day) or can act like a semi-permanent tatoo and remain on the skin for a about year or two or more.

In any event, whether the marking lasts for a short period of time or a longer period of time, the position or location of the ductal orifice can be recorded. The position or location can be relative to the topography of the nipple surface, a north-west-south east orientation or other landmarks on the body which can help identify the location of a tiny spot on the skin surface. Recording the location of the ductal orifice can be useful, e.g. to watch or monitor the duct, to facilitate treatment of an affected or suspect or high risk duct (e.g. affected with cancer or suspicious for cancer, or at high risk for cancer or cellular abnormality), or simply to retain a diagnostic or therapeutic history of that duct. Treatment of a duct can include, e.g. accessing a duct and/or removing all or a portion of it, or removing all or a portion of the epithelial lining of the duct.

After an orifice yields fluid upon nipple aspiration, the orifice can be contacted with a dilator (for example a dilator used in galactography procedures) in order to discern the precise location of the duct, discern the orientation of the duct (i.e. does it go straight in or in an angle), or to enlarge the orifice, e.g. by replacing the duct with dilators of successively larger diameter in order to dilate the orifice and early portion of the duct, so that access with an access tool might be easier.

The discovery of the invention is also that a nipple surface can be aspirated and at the first appearance of fluid, met with an action to collect the emerging fluid from the nipple surface before the fluid mixes with other fluid from other ducts. The fluid bead can be collected or retrieved by any suitable means or tool for doing so, e.g. with a small tube that pulls the fluid into it, e.g. a capillary tube. The fluid may be also collected, e.g. with an absorbent material that contacts the emerging bead and absorbs it. The importance of collecting the bead as it emerges from the orifice and not after the bead has mixed with fluid from any other orifice is that the fluid can be attributed to a single duct and as such can be analyzed independently of any other ducts on the breast. Thus, what can follow in the procedure once the nipple is aspirated and a fluid bead emerges and is collected from an orifice before it mixes with fluid from other ducts, is that the fluid can be analyzed and/or the ductal orifice where the bead emerges can be marked or the location of the orifice can be otherwise recorded as described herein for the purpose of keeping track of the status of the duct. For example, if the analysis of the ductal fluid indicates cancer or precancer a patient or clinician may choose to treat and/or monitor the duct and it would then be essential to be able to relocate with certainty the same duct from which the analyzed fluid was retrieved.

If the orifice and duct is accessed, the ductal contents may be retrieved from within the duct through the tool accessing the duct, and collected for analysis. A detection of abnormality in the cells, or of a particular marker or markers present in the ductal contents that indicate a warning sign for cancer, or detection of carcinoma itself may result from the analysis. In any event, the located and marked duct can be treated and/or monitored subsequent to the finding of high risk or other diagnosis.

The invention also provides a kit 100, as shown in FIG. 1, for differentiating a cancer risk status of breast ducts on a nipple comprising a nipple aspiration device 110 (e.g. any of those described herein), and a marking and/or recording system 200 to mark or record the location of any orifice that yields fluid from the nipple surface upon aspiration. The kit 100, illustrated in FIG. 1, will contain instructions 120 for use of the kit 100 to differentiate breast ducts on a nipple by cancer risk status using nipple aspiration to find a duct or ducts which yield fluid upon aspiration. The kit 100 can further comprise a ductal access tool 130, and instructions 132 for accessing a fluid yielding duct identified by the nipple aspiration procedure. The kit 100 can also contain one or more dilators 140 (for example galactography dilators) for dilating a ductal orifice before accessing the duct with a ductal access tool 130.

Figure 2:
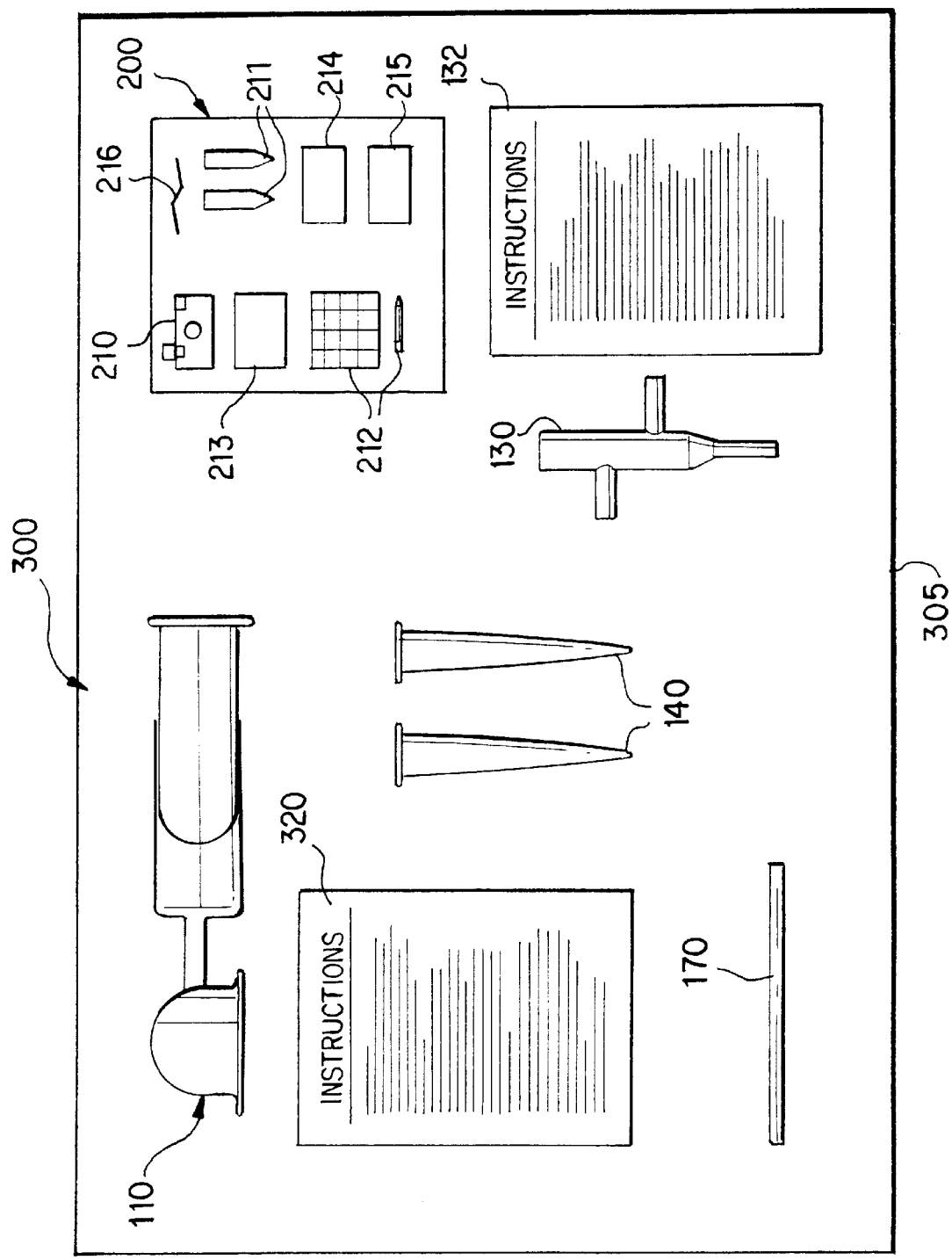
FIG. 2 illustrates a second embodiment of a kit for differentiating between a cancer risk status of a breast duct according to the present invention.
Figure 3:
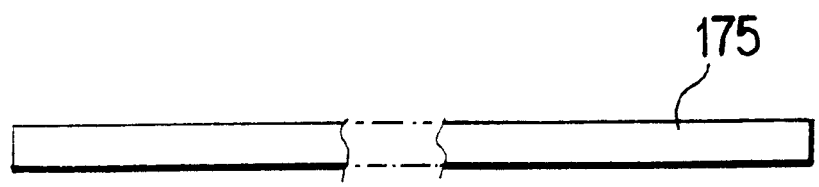
FIG. 3 illustrates a first embodiment of a tool according to the present invention for collecting ductal fluid from a nipple surface.
Figure 4:
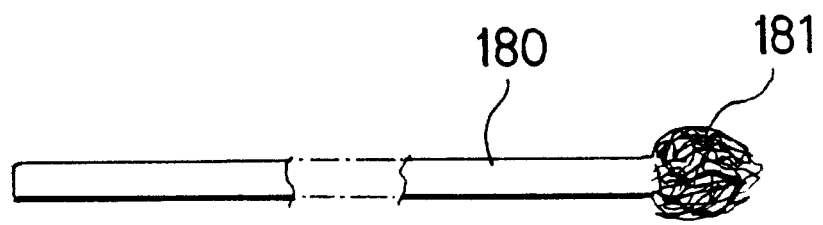
FIG. 4 illustrates a second embodiment of a tool according to the present invention for collecting ductal fluid from a nipple surface.

Alternatively the kit 300, shown in FIG. 2, can comprise a nipple aspiration device 110 and a ductal access tool 130 to access the duct and collect fluid for analysis. This kit 300 will also contain instructions 320 for aspirating the nipple to locate the ducts at risk, and accessing the ducts that yield fluid upon nipple aspiration. As shown in FIG. 2, the kit 300 can also contain the marking and/or recording tools 200 mentioned herein. The kit 300 containing the nipple aspiration device 110 can also include a means or tool 170 to collect an emerging bead of fluid off the nipple surface without mixing the fluid with fluid from any other duct on that nipple surface. The contained marking and/or recording tools 200 of either kit 100, 300 can be used for marking the location of ductal orifices so identified. The kit 300 may also contain one or more dilators 140: for example a galactography dilator or dilators. As discussed, any of the kits 100, 300 can have a marking and/or recording system 200, e.g. to locate any orifice that yields fluid upon aspiration, for example a camera 210, marking tool 211 (e.g. a pen or tattoo making tool), graph paper 212, a digital recording device 213, a digital imaging device 214, and/or a system 215 to make a negative imprint on the nipple surface and/or an element 216 to place in the orifice and duct to mark it (e.g. a plug, wire or tube). As discussed, any of the kits 100, 300 may contain the nipple aspiration device 110 and the ductal access tool 130, and any of the kits 100, 300 may contain a nipple aspiration device 110 and a tool 170 to collect an emerging bead of fluid at the ductal orifice, e.g. a tube 175 (e.g. a capillary tube), or a tool 180 having an absorbent tip 181 or an absorbent material that can contact the bead and absorb it as shown in FIGS. 3 and 4, respectively. The kits 100, 300 of the invention can further have a container 105, 305, respectively, for the kit contents as illustrated.

Sensitivity for differentiating a cancer risk status of milk ducts by aspirating the nipple can be further provided by maximizing the likelihood that ductal fluid already present in the duct will migrate to the nipple surface upon aspiration of the nipple. Maximizing the likelihood of migration of ductal fluid to the nipple surface can be accomplished by stimulating the breast and/or nipple surface. Stimulation of the breast and/or nipple surface can be accomplished e.g. by providing vibration at the nipple surface or at the breast as a whole. Vibration can be accomplished e.g. by placing a wearable device in contact with the nipple surface or breast for a period of time. The wearable device can provide continuous or intermittent vibration to the nipple or breast while being worn. The vibration can be provided for example by battery driven energy, or by a microchip controlled device. The device can be for example a bra-like item, or a patch affixed to the nipple.

The following examples are offered by way of illustration, not by way of limitation.

EXAMPLES

Example 1

A mammographically negative and physical exam negative woman was prepared for nipple aspiration on both her breasts. First the left nipple was aspirated, resulting in yield of a small amount of fluid from a ductal orifice at the nipple surface. The fluid was collected with a capillary tube without mixing the fluid with other portions of the nipple surface, and a small pen mark was placed at the site of the fluid yield and ductal orifice. The nipple was photographed, and the position of the ducts were marked on a grid. The duct yielding fluid was accessed subsequently and more ductal fluid was collected from within the duct. The nipple aspirate fluid collected in the capillary tube and the fluid collected from within the duct were analyzed separately for cancer markers and abnormal cell morphology. The procedure was repeated on the right breast in which two ductal orifices yielded fluid. The fluid was collected separately with a capillary tube, and the ductal orifices marked. The positions of the orifices were recorded on a grid, and the orifices were marked with a pen on the nipple surface. The ducts were accessed sequentially, and ductal fluid was retrieved from within the ducts and analyzed separately from each other and from the fluid collected in the capillary tubes.

Example 2

A female patient undergoes nipple aspiration on both breasts. The right breast yields two droplets at different locations on the nipple surface. The nipple surface at the droplets is marked with a skin marking pen (e.g. SHARPIE brand fine tip marker). Location B is marked with pen also, perhaps using a different color of SHARPIE (e.g. red or blue). Location A is proved with a ductal access tool (e.g. a catheter) and saline is infused into the duct. After the breast is massaged, ductal fluid is retrieved in the lumen of the catheter and collected in a collection tube using gentle aspiration at the lumen. The procedure is repeated at location B. The left breast yielded one droplet (location C) which is marked also with a SHARPIE pen, and the procedure of ductal access, fluid infusion, and withdrawal is repeated on the left breast.

Material (e.g. fluid, cells and/or other markers) from each duct A, B, and C is analyzed by cytology and for breast cancer specific markers in order to identify with precision the risk status of each duct for cancer or precancer, and ultimately to evaluate each breast of the patient for the presence of absence of breast cancer or precancer.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A kit for differentiating between a high cancer risk status or a low cancer risk status of milk ducts in a breast comprising:
   a nipple aspiration device,
   a system to mark and/or record the location of a ductal orifice that yields fluid upon aspiration, and
   instructions for use of the kit to identify a plurality of ducts as having either a high cancer risk status or a low cancer risk status and to differentiate between ducts identified as having the high cancer risk status and ducts identified as having the low cancer risk status by locating at least one ductal orifice that yields fluid upon aspiration.

2. A kit as in claim 1, further comprising a ductal access tool and further instructions to access the duct that yields fluid upon nipple aspiration.

3. A kit as in claim 2, further comprising a dilator.

4. A kit as in claim 1, wherein the system to mark and/or record the location of the ductal orifice that yields fluid upon aspiration comprises one or more of a pencil and graph paper, a camera, a marking tool, a digital recording and imaging device, a system to make a negative imprint on the nipple surface, and an element to place in the orifice to mark said orifice.

5. A kit for differentiating between a high cancer risk status or a low cancer risk status of milk ducts in a breast comprising:
  a nipple aspiration device,
  a ductal access tool to access a duct through a ductal orifice that yields fluid upon nipple aspiration, and
  instructions for use of the kit to identify a plurality of ducts as having either a high cancer risk status or a low cancer risk status, to differentiate between ducts identified as having the high cancer risk status and ducts identified as having the low cancer risk status by locating at least one ductal orifice that yields fluid upon nipple aspiration and to access the duct through an orifice thereof.

6. A kit as in claim 5, further comprising a dilator.

7. A kit for differentiating between a high cancer risk status or a low cancer risk status of milk ducts in a breast comprising:
  a nipple aspiration device,
  a tool to retrieve an emerging bead of fluid at a ductal orifice,
  instructions for use of the kit to identify a plurality of ducts as having either a high cancer risk status or a low cancer risk status and to differentiate between ducts identified as having the high cancer risk status and ducts identified as having the low cancer risk status by locating at least one ductal orifice that yields fluid upon nipple aspiration and
  instructions for collecting an emerging bead of fluid at the ductal orifice without mixing the collected fluid with any other fluid yielded from any other duct.

8. A kit as in claim 6, further comprising a dilator.

9. A method for screening women for breast cancer, said method comprising the steps of:
  aspirating a nipple until an identifiable amount of ductal fluid is located at one or more ductal openings on a surface of said nipple;
  differentiating between higher cancer risk ducts and lower cancer risk ducts in the breast in response to said aspirating step;
  identifying each duct as having either a high cancer risk status or a low cancer risk status; and
  accessing at least one duct that has been identified as having a high cancer risk status.

10. The method of claim 9 wherein the aspirating step includes the steps of positioning an aspirator cup over said nipple, and creating a negative pressure within said cup.

11. The method of claim 9 wherein the differentiating step includes identifying ductal orifices that have yielded fluid.

12. The method of claim 11 wherein said identifying step includes identifying each duct that yields fluid as having a high cancer risk status.

13. The method of claim 12 further including the step of marking the location of each ductal opening that yields ductal fluid.

14. The method of claim 9 further including the step of recording the location of each ductal opening that yields ductal fluid.

15. The method of claim 14 wherein said recording step comprises at least one of the following steps: indicating the location of each duct that yields fluid on a paper grid, capturing an image of the nipple surface, and making an imprint of the nipple surface.

16. The method of claim 9 wherein said method includes the step of collecting the fluid from each of a plurality of said ducts prior to said fluid from said plurality of said ducts mixing together.

17. The method of claim 9 further comprising the step of retrieving material from each accessed high risk duct.

18. The method of claim 9 further comprising the step of marking each ductal opening on the nipple surface that yields fluid.

19. The method of claim 18 wherein said marking step includes placing an identifiable mark on said nipple surface to identify the location of each ductal opening that yields fluid using a pen or a labeling device.

20. The method of claim 18 wherein said marking step includes introducing a removable element into each ductal opening that yields fluid.

21. The method of claim 20 wherein the removable element is selected from the group consisting of a plug, a tube, a wire, a thread and a suture.

22. A method for screening women for breast cancer, said method including the steps of:
  aspirating a nipple of a breast;
  differentiating between high cancer risk ducts and low cancer risk ducts of the breast in response to said aspirating step;
  identifying each duct as having either a high cancer risk status or a low cancer risk status; and
  accessing at least one duct identified as having a high cancer risk status through a ductal opening.

23. The method of claim 22 wherein said differentiating step includes visually observing an initial amount of aspirated ductal fluid on a surface of said nipple, and said identifying step includes identifying each duct that yields said observed ductal fluid as having a high cancer risk status.

24. The method of claim 23 wherein the observed ductal fluid from each duct is removed from the nipple surface prior to the ductal fluid from two or more ducts mixing together.

25. The method of claim 23 further including the step of recording the location of each ductal opening that yields ductal fluid.

26. The method of claim 25 wherein said recording step comprises at least one of the following steps: indicating the location of each duct that yields fluid on a paper grid, capturing an image of the nipple surface, and making an imprint of the nipple surface.

27. The method of claim 23 wherein said method includes the step of collecting the fluid from each of a plurality of said ducts prior to said fluid from said plurality of said ducts mixing together.

28. The method of claim 22 further comprising the step of retrieving material from each accessed high risk duct.

29. The method of claim 22 further comprising the step of marking each ductal opening on the nipple surface that yields fluid.

30. The method of claim 29 wherein said marking step includes placing an identifiable mark on said nipple surface to identify the location of each ductal opening that yields fluid using a pen or a labeling device.

31. The method of claim 29 wherein said marking step includes introducing a removable element into each ductal opening that yields fluid.

32. The method of claim 31 wherein the removable element is selected from the group consisting of a plug, a tube, a wire, a thread and a suture.

* * * * *